(12) United States Patent
Friedman

(10) Patent No.: US 6,669,693 B2
(45) Date of Patent: Dec. 30, 2003

(54) TISSUE ABLATION DEVICE AND METHODS OF USING

(75) Inventor: Paul Friedman, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 10/008,005

(22) Filed: Nov. 13, 2001

(65) Prior Publication Data

US 2003/0093072 A1 May 15, 2003

(51) Int. Cl.$^7$ .............................................. A61B 18/18
(52) U.S. Cl. ....................................... 606/41; 607/122
(58) Field of Search ..................... 606/41, 42, 48–50; 607/101, 102, 122

(56) References Cited

U.S. PATENT DOCUMENTS

| | | | |
|---|---|---|---|
| 5,053,008 A | | 10/1991 | Bajaj |
| 5,125,928 A | * | 6/1992 | Parins et al. ................. 606/48 |
| 5,327,889 A | * | 7/1994 | Imran ......................... 600/373 |
| 6,029,091 A | * | 2/2000 | de la Rama et al. ......... 607/102 |
| 6,068,629 A | * | 5/2000 | Haissaguerre et al. ........ 606/41 |
| 6,164,283 A | | 12/2000 | Lesh |
| 6,197,022 B1 | * | 3/2001 | Baker ........................... 606/33 |
| 6,214,002 B1 | | 4/2001 | Fleischman et al. |
| 6,237,606 B1 | | 5/2001 | Zikorus et al. |
| 6,254,599 B1 | | 7/2001 | Lesh et al. |
| 6,258,087 B1 | * | 7/2001 | Edwards et al. .............. 606/41 |
| 6,315,778 B1 | | 11/2001 | Gambale et al. |
| 6,398,780 B1 | * | 6/2002 | Farley et al. ................. 606/41 |

FOREIGN PATENT DOCUMENTS

EP   1 042 990 A1   10/2000

OTHER PUBLICATIONS

Asirvatham and Friedman, "Ablation for Atrial Fibrillation: Is the Cure at Hand?" *J. Cardiovasc. Electrophysiol.*, 2001, 12:909–911.

Ernst et al., "Modification of the Substrate for Maintenance of Idiopathic Human Atrial Fibrillation," *Circulation*, 1999, 100:2085–2092.

Ernst et al., "Prevention of Atrial Fibrillation by Complete Compartmentalization of the Left Atrium Using a Catheter Technique," *J. Cardiovasc. Electrophysiol*, 2000, 11:686–690.

(List continued on next page.)

*Primary Examiner*—Michael Peffley
(74) *Attorney, Agent, or Firm*—Fish & Richardson P.C., P.A.

(57) ABSTRACT

The invention provides for a tissue ablation device and methods of using such a tissue ablation device for treating cardiac arrhythmias.

50 Claims, 16 Drawing Sheets

OTHER PUBLICATIONS

Haines, "The Biophysics of Radiofrequency Catheter Ablation in the Heart: The Importance of Temperature Monitoring," *PACE,* 1993, 16 (Part II):586–591.

Haissaguerre et al., "Spontaneous Initiation of Atrial Fibrillation by Ectopic Beats Originating in the Pulmonary Veins," *N. Engl. J. Med.,* 1998, 339:659–666.

Haissaguerre et al., "Electrophysiological End Point for Catheter Ablation of Atrial Fibrillation Initiated from Multiple Pulmonary Venous Foci," *Circulation,* 2000, 101:1409–1417.

Haissaguerre et al., "Catheter Ablation of Chronic Atrial Fibrillation Targeting the Reinitiating Triggers," *J. Cardiovasc. Electrophysiol.,* 2000, 11:2–10.

Haissaguerre et al., "Incidence and Topography of Foci Triggering Atrial Fibrillation after Successful Pulmonary Vein Disconnection," *PACE,* 2001, 24(4):540, Abstract #7.

Natale et al., "First Human Experience with Pulmonary Vein Isolation Using a Through–the–Balloon Circumferential Ultrasound Ablation System for Recurrent Atrial Fibrillation," *Circulation,* 2000, 102:1879–1882.

Pappone et al., "Circumferential Radiofrequency Ablation of Pulmonary Vein Ostia," *Circulation,* 2000, 102:2619–2628.

Wittkampf et al., "Myocardial Temperature Response During Radiofrequency Catheter Ablation," *PACE,* 1995, 18:307–317.

* cited by examiner

TISSUE ABLATION DEVICE AND METHODS OF USING

TECHNICAL FIELD

This invention relates to cardiac arrhythmias, and more particularly to a tissue ablation device and methods of using such a device.

BACKGROUND

Atrial fibrillation is the most common sustained arrhythmia encountered in clinical practice and affects over 2 million Americans. Atrial fibrillation is often initiated by rapidly firing triggers located in the pulmonary veins. One method for treating atrial fibrillation includes placement of a catheter adjacent to the arrhythmogenic substrate that contains the trigger or electrically connects the trigger to the atrium, followed by subsequent ablation of the tissue containing the trigger. These triggers may only discharge intermittently, which makes it difficult to precisely position the catheter with respect to the trigger location and precisely ablate the tissue necessary to eradicate the trigger.

The anatomy of the pulmonary veins is complex, and technical limitations make localizing and eliminating pulmonary vein potentials difficult. Multiple procedures, therefore, are often required to precisely locate the triggers in the pulmonary veins. Once the triggers are located, complications often arise during the ablation procedure. For example, ablation within the pulmonary vein increases the risk of pulmonary vein stenosis. In addition, effective monitoring of the pulmonary vein (e.g., assessment of edema, thrombosis, and/or narrowing) during energy delivery remains difficult.

SUMMARY

Conventional catheters, including a Laso catheter and various balloon catheters, have been used in both diagnostic and therapeutic applications. However, using these conventional catheters it is difficult to engage the target tissue, either circumferentially or focally. These devices also have a propensity for entering the pulmonary vein, which has further limited their usefulness in the treatment of atrial fibrillation.

The invention provides for a tissue ablation device having a retractable and deployable umbrella body. The umbrella body includes ablation elements for circumferentially engaging and ablating a target tissue. The invention further provides of methods of using such a tissue ablation device for treating cardiac arrhythmias.

The umbrella body is an adjustable, compliant cone-shaped member that may be deployed over a wide range of working diameters. The ablation elements attached to the umbrella body can therefore conform to the geometry of the pulmonary vein ostium and provide circumferential contact, which permits more accurate ablation procedures.

The deployable umbrella body allows the tissue ablation device of the invention to be configured in a wide variety of ways. For example, the ablation elements on such a device can be configured for circumferential, focal or segmental ablation. In addition, the device may be used to simultaneously record pulmonary vein potentials from various depths within the vein to facilitate determination of successful ablation. The adjustable deployment of an umbrella body allows for a wide variety of patients or of vessels within a single patient to be treated with just one or a few tissue ablation devices.

In one aspect, the invention provides for a tissue ablation device including a catheter body and at least one deployable umbrella body attached to the distal portion of the catheter body. Generally, the catheter body has a proximal portion and a distal portion, wherein the proximal and distal portions define a longitudinal axis. The umbrella body generally includes a plurality of radial splines and at least one ablation element, wherein the at least one ablation element is attached to at least one of the plurality of splines. Each of the splines typically has a distal end and a hinged end, wherein the hinged end is attached to the catheter body.

A tissue ablation device of the invention can further include a deployment element connected to the splines, wherein the deployment element is capable of adjustably deploying the umbrella body. Ablation elements can be attached to the splines at the distal end of the splines or at a position medial to the distal end and the hinged end of the spline. A deployment element can include a slideable deployment/retractor collar that circumscribes the splines and can further include connector rods linking the slideable deployment/retractor collar to the splines. A tissue ablation device of the invention can have a deployment element that includes a slideable deployment/retractor collar circumscribing the splines, which further include a deployment member for adjustably sliding the deployment/retractor collar along the longitudinal axis of the catheter body. A tissue ablation device of can have a deployment member that comprises a slideable member that is a contiguous body with the splines. In one embodiment, the slideable member is within a central lumen of the catheter body. According to the invention, the hinged end of the splines can be attached to the catheter body or can be attached to a central hub on the catheter body.

An umbrella body on a tissue ablation device of the invention can further comprise at least one circumferential loop or loop segment attached to the plurality of splines. An umbrella body can include one or more (e.g., two) circumferential loop attached to the plurality of splines. According to the invention, a loop segment can be a contiguous member of the spline. Further, loop segments can be hinged. In addition, circumferential loops or loop segments can be conductive, or can have ablation elements attached to at least one of the circumferential loops or loop segments. An umbrella body can further comprise membranous material attached to one or more sets of adjacent splines. Such membranous material can comprise at least one ablation element or itself can be conductive.

It is a feature of the invention that the distal ends of the splines can move through an angle α relative to the longitudinal axis of the catheter body. The angle α can be between about 0° and about 90° or between about 0° and about 180° relative to the longitudinal axis of the catheter body.

An ablation element suitable for use in the invention can be a cryogenic element, an ultrasound element, a light-emitting element, a microwave element, a thermal element, a laser, chemical fluid, or an electrode element. According to the invention, the ablation element can be an electrode. An electrode can be a band electrode, a spiral electrode, or a coil electrode.

A tissue ablation device of the invention can further include at least one of a monitoring device or a sensing element attached to the tissue ablation device. Representative monitoring devices and/or sensing elements include an intracardiac echo device, an ultrasound transducer assembly attached to the tissue ablation device, and electrodes.

In another aspect, the invention provides a tissue ablation device for treating atrial arrhythmia, can include a catheter body, wherein the catheter body with a proximal portion and a distal portion, wherein the proximal and distal portions define a longitudinal axis; and at least one deployable umbrella body located at the distal portion of the catheter body, wherein the umbrella body comprises. An umbrella body includes a plurality of splines attached to the catheter body, and at least one ablation element, wherein the at least one ablation element is attached to at least one of the plurality of splines. According to the invention, the splines can be radially deployed to fit the size of the pulmonary vein ostium.

In another aspect of the invention, there is provided a method for treating arrhythmia, including providing a tissue ablation device, wherein the device comprises: a catheter body having a proximal portion and a distal portion, wherein the proximal and distal portions define a longitudinal axis; and at least one deployable umbrella body attached to the distal portion of the catheter body, wherein the umbrella body comprises a plurality of splines attached to the catheter body, and at least one ablation element, wherein the at least one ablation element is attached to at least one of the plurality of splines, wherein the umbrella body is adapted to be delivered to a patient's vasculature in a retracted configuration and is adapted to contact a circumferential region of tissue at a pulmonary vein ostium in a deployed configuration; inserting and advancing the distal end of the catheter body into the vasculature of an individual experiencing arrhythmia; positioning and deploying the umbrella body such that the plurality of splines are circumferentially disposed at the tissue of a pulmonary vein ostium; and activating the ablation element. Such a method can be used for treating atrial fibrillation, atrial tachycardia, and atypical atrial flutters. Generally, the arrhythmia originates at least in part from an arrhythmogenic origin located at or near the pulmonary vein ostium or other venous structure.

According to the invention, ablation elements can be a cryogenic element, an ultrasound element, a light-emitting element, a microwave element, a thermal element, a laser, chemical fluid, or an electrode element. Specifically, an ablation element can be an electrode. An electrode can deliver a radiofrequency signal of, for example, a 500 KHz or a 250 KHz radiofrequency signal for about 30 to about 120 seconds. Electrodes on a tissue ablation device of the invention can deliver a radiofrequency signal at a temperature of about 40° C. to about 70° C. Because of their configuration, ablation elements can be activated in a focal, segmental or circumferential manner. Methods of the invention also can utilize a monitoring device or sensing elements located on the tissue ablation device. Signals emitted from the monitoring device or sensing elements can be out of phase with signals emitted from the ablation elements.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

Like reference symbols in the various drawings indicate like elements.

DETAILED DESCRIPTION

Figure 1A:
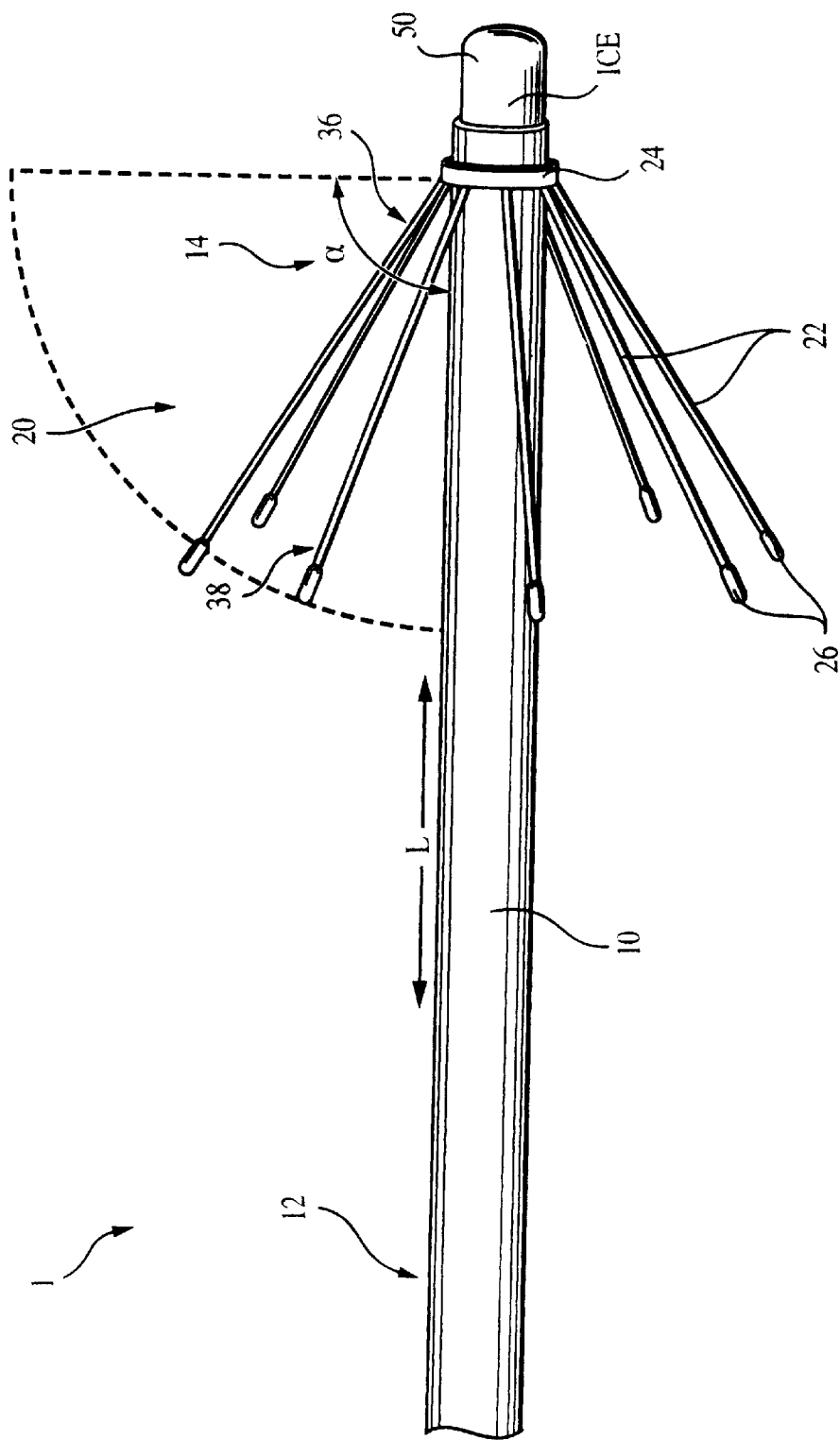
FIGS. 1A and 1B are images showing embodiments of a tissue ablation device of the invention in which the umbrella body is deployed.

Referring to FIG. 1A, an embodiment of a tissue ablation device 1 is shown that includes a catheter body 10 and one umbrella body 20. The catheter body 10 includes a proximal portion 12 and a distal portion 14 along a longitudinal axis L of the device 1. The catheter body 10 is generally tubular and can contain a central lumen (not shown in FIG. 1A) that can be used for carrying any wires or connectors suitable for operation of the device.

Figure 1B:
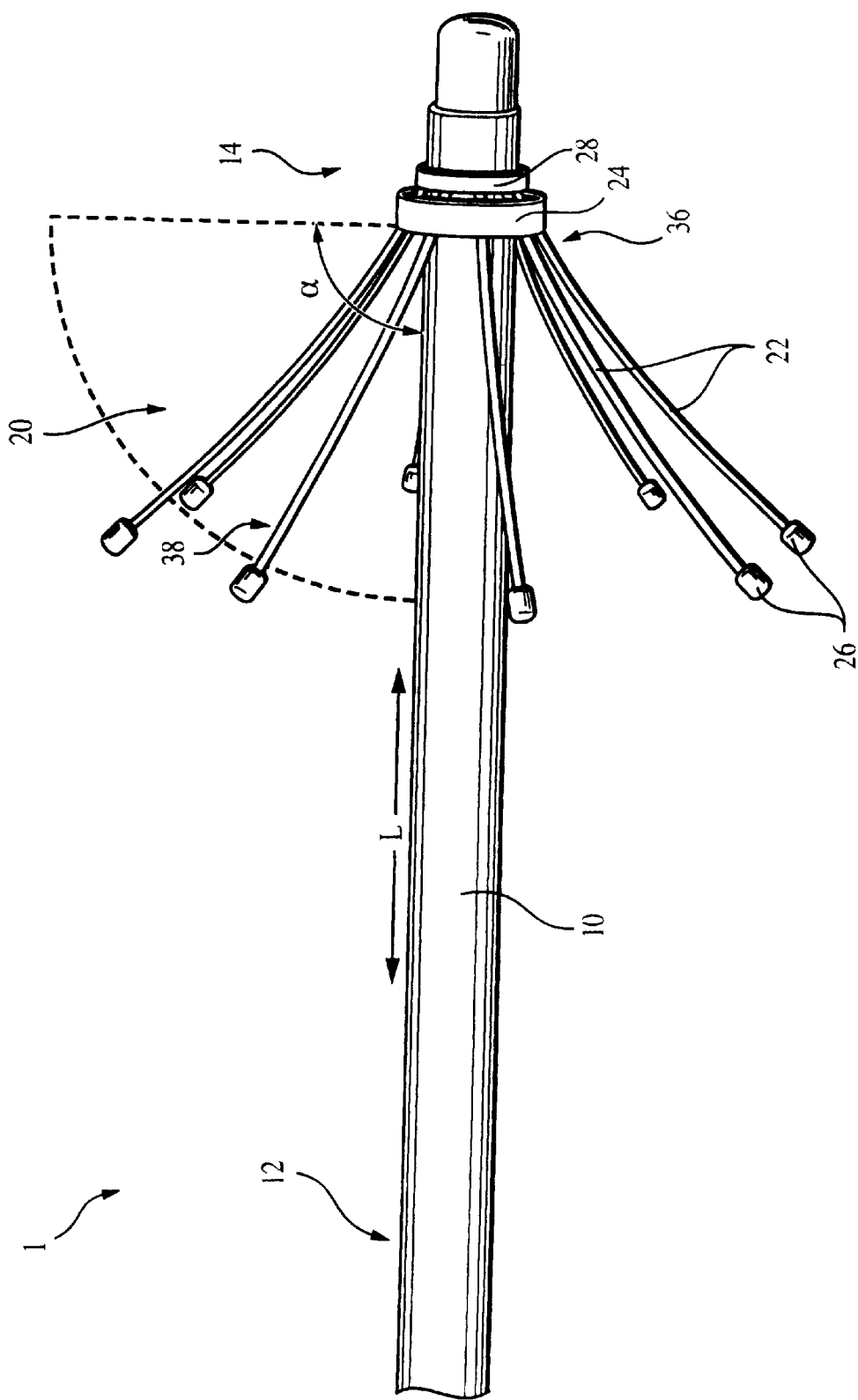
Figure 1C:
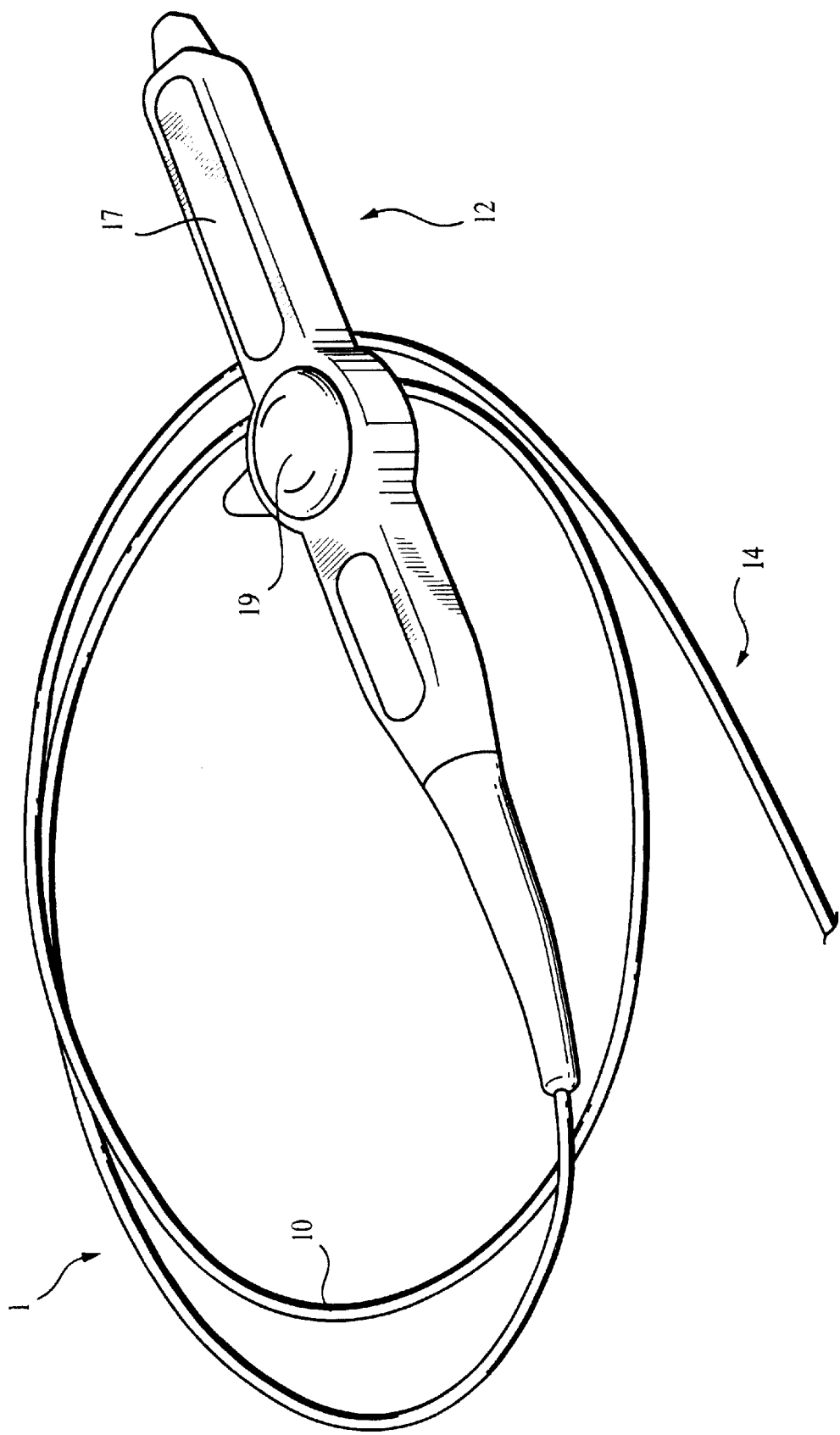
FIG. 1C is an image showing a representative handle of a tissue ablation device.

Referring to FIG. 1C, the proximal portion 12 of the catheter body 10 typically contains a handle 17 to be grasped by a user. Configurations and elements required of a catheter handle are well known in the art. A proximal portion of a catheter body can further contain a mechanism 19 to be manipulated by the user to deploy and retract the umbrella body 20. The mechanism to deploy and retract the umbrella body 20 will depend on the configuration of the umbrella body or bodies and the catheter body 10.

The proximal 12 and distal 14 portions of the catheter body 10 can be integrally formed from a biocompatible material having requisite strength and flexibility for introducing and advancing the tissue ablation device 1 of the invention into the vasculature of an individual. The proximal 12 and distal 14 portions can be flexible to facilitate articulation of a tissue ablation device 1 during use. Appropriate materials are well known in the art and generally include polyamides such as, for example a woven material available from DuPont under the trade name Dacron. Although not specifically shown, the catheter body may be configured for an over-the-wire or through-a-sheath application.

Referring again to FIG. 1A, the umbrella body 20 is circumferentially arranged about the distal portion 14 of the catheter body 10. The umbrella body 20 includes a plurality of circumferentially disposed radial splines 22 whose free end can extend outward from the catheter body 10. In the embodiment illustrated in FIG. 1A, the splines 22 are generally rod-like structures with a hinged end 36 attached directly to the outside of the catheter body 10. The distal free end 38 of a spline 22 is free to swing through an arc at an angle α with respect to the longitudinal axis L of the catheter body 10. The angle α can range from about 0°, in which a spline 22 is retracted and generally aligned with the longitudinal axis L of the catheter body 10, and about 90°, in which a spline 22 is fully deployed and lies in a plane perpendicular to the longitudinal axis L of the catheter body 10. The hinged end 36 of a spline 22 is configured such that the distal end 38 of a spline 22 can assume a variety of positions along this arc relative to the longitudinal axis L of a catheter body 10. The various positions that multiple circumferentially disposed splines 22 can assume during deployment provide a total cone-shaped or frustum-shaped umbrella body 20 that undergoes an increase in surface area as the umbrella body is deployed.

The movement and position of the splines 22 with respect to the longitudinal axis L of the catheter body 10 can be adjustably controlled by a variety of different means. A slideable deployment/retraction collar 24 that circumscribes the catheter body 10 is shown in FIG. 1A. An ablation device of the invention would be introduced into vasculature in a retracted position in which a slideable collar 24 such as that shown in FIG. 1A circumscribes the splines 22 at their distal ends 38. During deployment, the collar 24 can be adjustably moved toward the hinged end 36 of the splines 22. Movement of the collar 24 toward the hinged end 36 of the splines 22 causes the distal ends 38 of the splines to move through the arc a from a retracted position (i.e., essentially parallel to the longitudinal axis of L of the catheter body 10 or about 0°) to any desired angle α with respect to the longitudinal axis L of the catheter body 10. The collar 24 then engages the splines 22 during retraction and slides along the longitudinal axis L of the catheter body 10 toward the distal ends 38 of the splines 22 from the deployed position shown back to a position essentially parallel with the catheter body 10.

The configuration shown in FIG. 1A for deployment/retraction requires that either or both the hinged end 36 of the spline 22, or the spline itself, must have an inherent or natural propensity for the deployed position. Splines 22 can be made from a rigid material (see, for example, FIG. 1A) or a material that allows, for example, a bowed spline as shown in FIG. 1B. For example, splines 22 can be constructed using materials known in the art such as polyethylene. The length of a spline 22 can vary and will depend on the configuration of the umbrella body including the materials used to make the splines and the mechanism of deployment and retraction.

An umbrella body can include ablation elements 26. The terms "ablate" or "ablation," including derivatives thereof, refers to the substantial alteration of the mechanical, electrical, chemical, or other structural nature of tissue. In the context of intracardiac ablation as shown and described with reference to the various embodiments of the invention, "ablation" refers to sufficient altering of tissue properties to substantially block conduction of electrical signals from or through the ablated cardiac tissue. The term "element" within the context of "ablation element" refers to a discrete element, such as an electrode. Therefore, as used herein, "ablation elements" according to the defined terms may include one or more specific structures adapted to ablate a defined region of tissue.

For example, an ablation element suitable for use in the invention may be an energy emitting type that is adapted to emit energy sufficient to ablate tissue when coupled to and energized by an appropriate energy source. Accordingly, ablation elements suitable for use in the invention can include, for example: an electrode element adapted to couple to a direct current ("DC") or alternating current ("AC") source, such as a radiofrequency ("RF") current source; an antenna element which is energized by a microwave energy source; a heating element such as a metallic element or other thermal conductor which is energized to emit heat such as by convective or conductive heat transfer, by resistive heating due to current flow, or by optical heating with light; a light emitting element such as a fiber optic element which transmits light sufficient to ablate tissue when coupled to a light source; or an ultrasonic element such as an ultrasound crystal element which is adapted to emit ultrasonic sound waves sufficient to ablate tissue when coupled to a suitable excitation source. See, for example, WO 93/20767, and U.S. Pat. Nos. 5,104,393 and 5,575,766. In addition, other elements for altering the nature of tissue may be suitable for use as "ablation elements" in a tissue ablation device of the invention. For example, a cryoablation element adapted to sufficiently cool tissue to thereby alter the structure thereof can be suitable for use in the current invention. Further, a fluid delivery element such as a discrete port or a plurality of ports which are coupled to a fluid delivery source can be adapted to infuse an ablating fluid, such as a fluid containing alcohol, into the tissue to alter the nature of the tissue.

In one embodiment, ablation elements can be electrodes delivering radiofrequency signals. Electrodes on splines or circumferential loop segments can be, for example, band electrodes, spiral electrodes, or coil electrodes. In addition, electrodes of various sizes can be used. Traditionally, small electrodes have been used for tissue ablation. Ablation using a small electrode is sometimes difficult, however, due to an "edge effect" in which most or all of the energy is focused on the edge of the electrode. The edge effect can be overcome by using a larger electrode with more surface area (see, for example, ablation element 26 in FIG. 7E). A lower radiofrequency signal also can be used to improve the ablative effect of an electrode. For example, instead of a 500 kHz radiofrequency signal that is often used for tissue ablation, a 250 kHz signal can be used. Adjustments in the size and position of ablation elements, as well as in the energy source may be required for optimal tissue ablation using a device of the invention.

Figure 2:
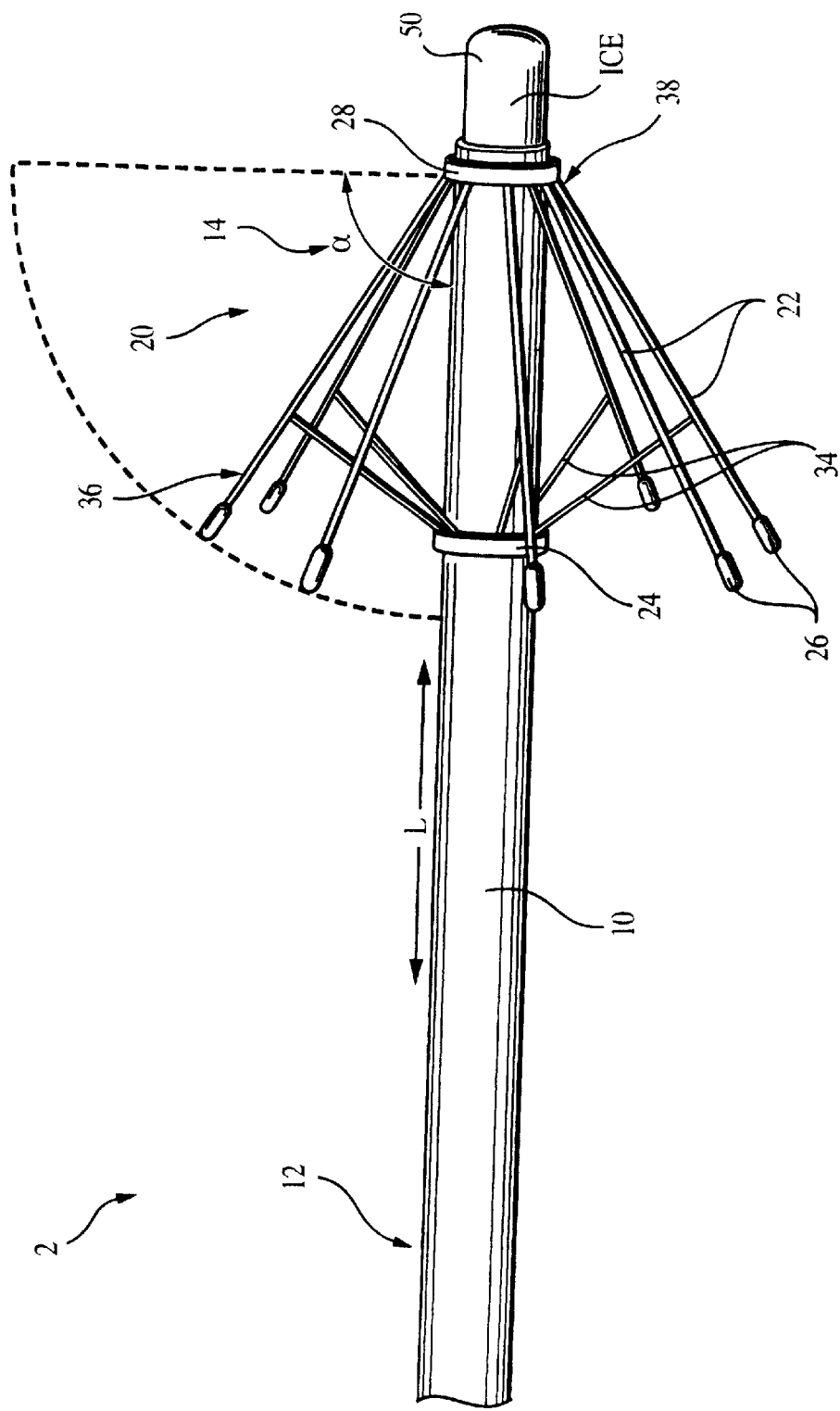
FIG. 2 is an image showing an embodiment of a tissue ablation device of the invention in which the umbrella body is deployed.

Various patterns of ablation elements 26 attached to splines 22 can be used. For example, ablation elements on splines can be located at the distal end of the splines 38 as shown in FIGS. 1A, 1B, and 2. Ablation elements on splines can be located at any operable position between the distal end 38 and the hinged end 36 (see, for example, FIGS. 7A–E). Ablation elements 26 can be configured as a series of separate ablation elements that can be isolated from one another for focal ablation or, alternatively, some or all of the ablation elements can be connected to one another for focal, segmental, and/or circumferential ablation.

The number and position of splines 22 as well as the manner in which a hinged end 36 of a spline is attached to a catheter body can vary, and can be dependent at least in part on the mechanism by which the umbrella body 20 is deployed and retracted. The splines 22 can be attached to the catheter body 10 by any number of methods. For example, in addition to the direct attachment mechanism shown in FIG. 1A, the embodiment shown in FIG. 1B demonstrates that the splines 22 can be attached to a central hub 28 that circumscribes the catheter body 10. As in FIG. 1A, the movement and position of the splines 22 with respect to the longitudinal axis L of the catheter body 10 can be precisely controlled by the slideable deployment/retraction collar 24.

Referring to FIG. 2, an ablation device 2 is shown that includes a catheter body 10 and an umbrella body 20. A central hub 28 circumscribes a catheter body 10, and includes a radial arrangement of splines 22. A slideable deployment/retractor collar 24 also circumscribes the catheter body 10 and can move along the longitudinal axis L thereof. The deployment/retractor collar 24 includes a circumferential arrangement of connector rods 34 attached to the splines 22. The deployment/retractor collar 24 and the connector rods 34 can be configured such that the deployment/retractor collar 24 moves toward the proximal portion 12 of the catheter body for retraction from the deployed position shown or, alternatively, such that the deployment/retractor collar 24 moves toward the distal portion 14 of the catheter body for retraction.

Figure 3A:
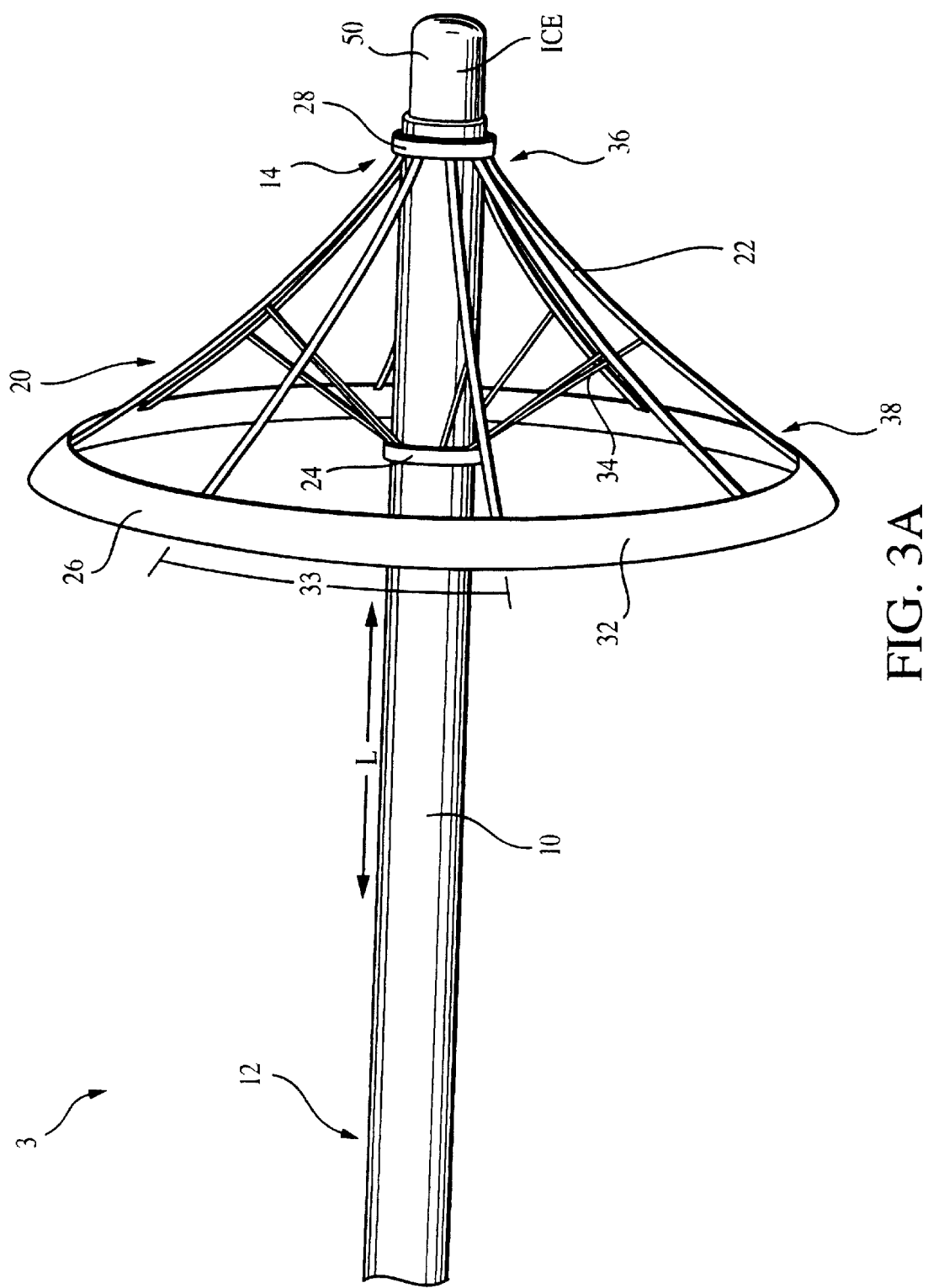
FIGS. 3A and 3B are images showing embodiments of a tissue ablation device of the invention in which the umbrella body includes a single circumferential loop (FIG. 3A) or multiple circumferential loops (FIG. 3B).

Referring to FIG. 3A, an ablation device 3 is shown that includes a slideable deployment/retractor collar 24 that circumscribes the catheter body and is attached to connector rods 34 that engage a circumferential array of splines 22 forming an umbrella body 20. In this embodiment, the umbrella body includes a circumferential loop 32. The circumferential loop 32 is made up of loop segments 33 that connect adjacent splines 22 in the umbrella body 20. The circumferential loop 32 can be made of conductive material, can contain ablation elements, can be for structural support of the umbrella body, and/or can play a mechanistic role (e.g., in deployment or retraction). Advantageously, circumferential loops 32 that are conductive (see, for example, FIG. 3A) or that contain ablation elements provide more surface area for contacting and ablating target tissue. Ablation elements 26 can be attached to circumferential loops 32 or loop segments 33 and can be at any position on the circumferential loop or loop segment and in any pattern. In the embodiment shown in FIG. 3A, the circumferential loop 32 is located at the distal end of the splines 22 with loop segments 33 that connect each spline to an adjacent spline. The circumferential loop, however, need not be completely contiguous around the entire circumference of an umbrella body (see, for example, FIG. 7B) and the loop segments 33 need not connect every pair of adjacent splines. The adjacent splines 22 can be connected by a circumferential loop 32 or loop segments 33 at various positions along the lengths of the splines.

Figure 3B:
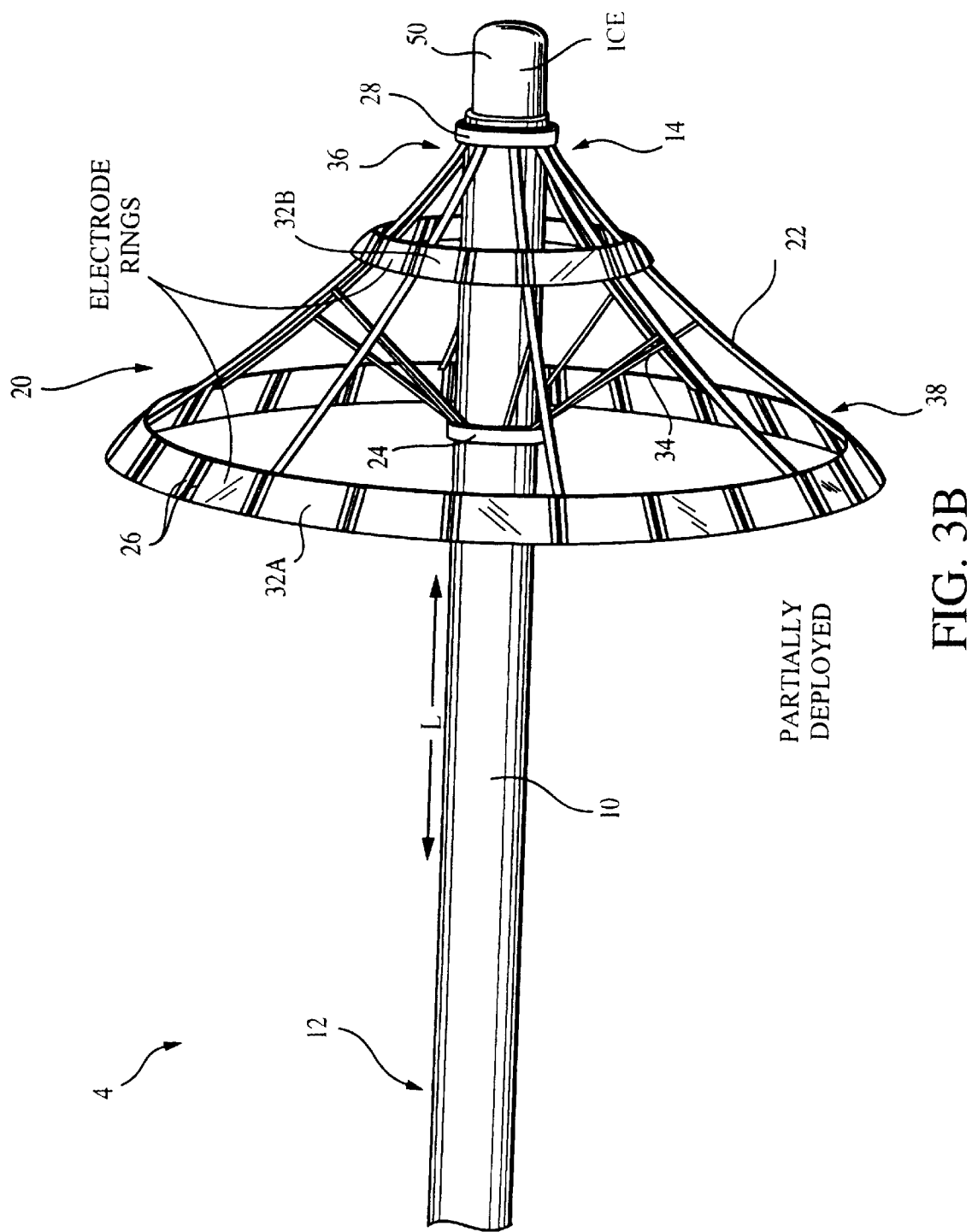

Referring to FIG. 3B, an ablation device 4 is shown that includes multiple circumferential loops. In this embodiment, the umbrella body 20 includes a first circumferential loop 32A at the distal end of the splines and a second circumferential loop 32B medial to the distal ends and the hinged ends of the splines. The use of multiple circumferential loops offers increased surface area for ablation elements, increased support for the umbrella body, and increased range of diameters available on a single umbrella body of engaging the target tissue. The use of proximal and distal loops also permits monitoring of the pulmonary vein potentials at various positions along the vein, and specifically, monitoring potentials within the vein from a distal loop while ablating ostially. The circumferential loops shown in FIGS. 3A and 3B would requisitely fold up or collapse in on themselves as the umbrella body is retracted.

The circumferential loops 32 or loop segments 33 can be made using an inert structural material such as polyethylene, a conductive material, or a material with memory such as, for example, nickel/titanium alloys such as those available from Unitek Corporation under the trade name Nitinol. The circumferential loops 32 can include one or more shapes, and may be for example circular, oblong, ovular, or elliptical. The terms "circumference" or "circumferential", including derivatives thereof, are herein intended to mean a path or line that forms an outer border or perimeter that surrounds and thereby defines an enclosed circular or circular-like region of space. The path or line defining such a circumferential loop can be an imaginary line connecting multiple points (e.g., the distal ends of splines) or a contiguous (e.g., circumferential loops) or discontiguous (e.g., loop segments) physical connection. The related term "circumscribe," including derivatives thereof, is herein intended to mean to enclose, surround, or encompass a defined region of space.

Figure 4:
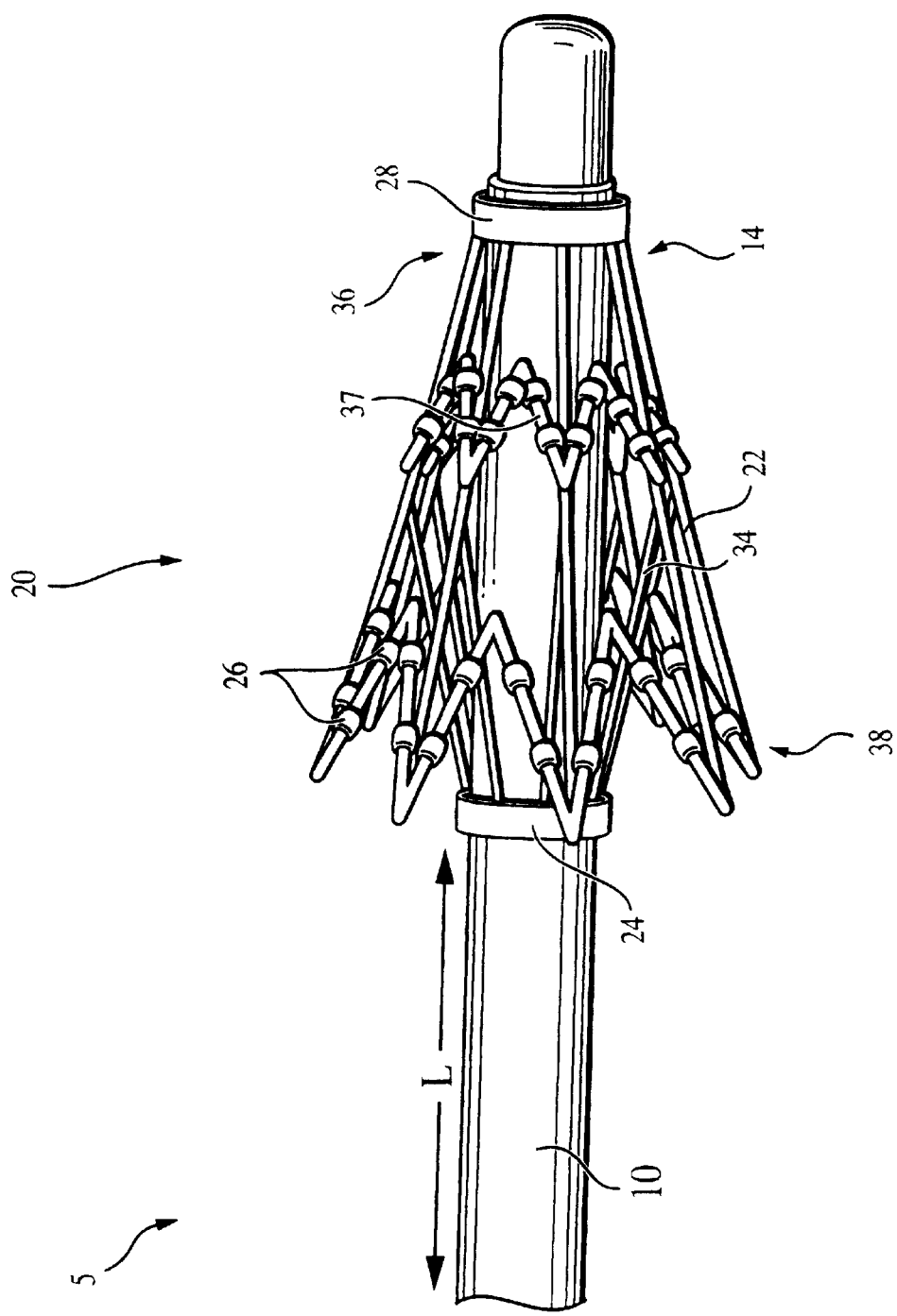
FIG. 4 is an image showing an embodiment of a tissue ablation device of the invention in which the umbrella body is retracted.

Referring to FIG. 4, an ablation device 5 is shown that includes a catheter body 10 and an umbrella body 20. Similar to the embodiment shown in FIG. 2, the umbrella body 22 shown in FIG. 4 has a central hub 28 to which the circumferentially disposed splines 22 are attached. For deployment and retraction, connector rods 34 connect the splines 22 to a slideable deployment/retractor collar 24 that circumscribes the catheter body 10. The umbrella body shown in FIG. 4 further includes loop segments 37 with medial hinges 37A for deployment and/or retraction of the umbrella body 22.

Figure 5:
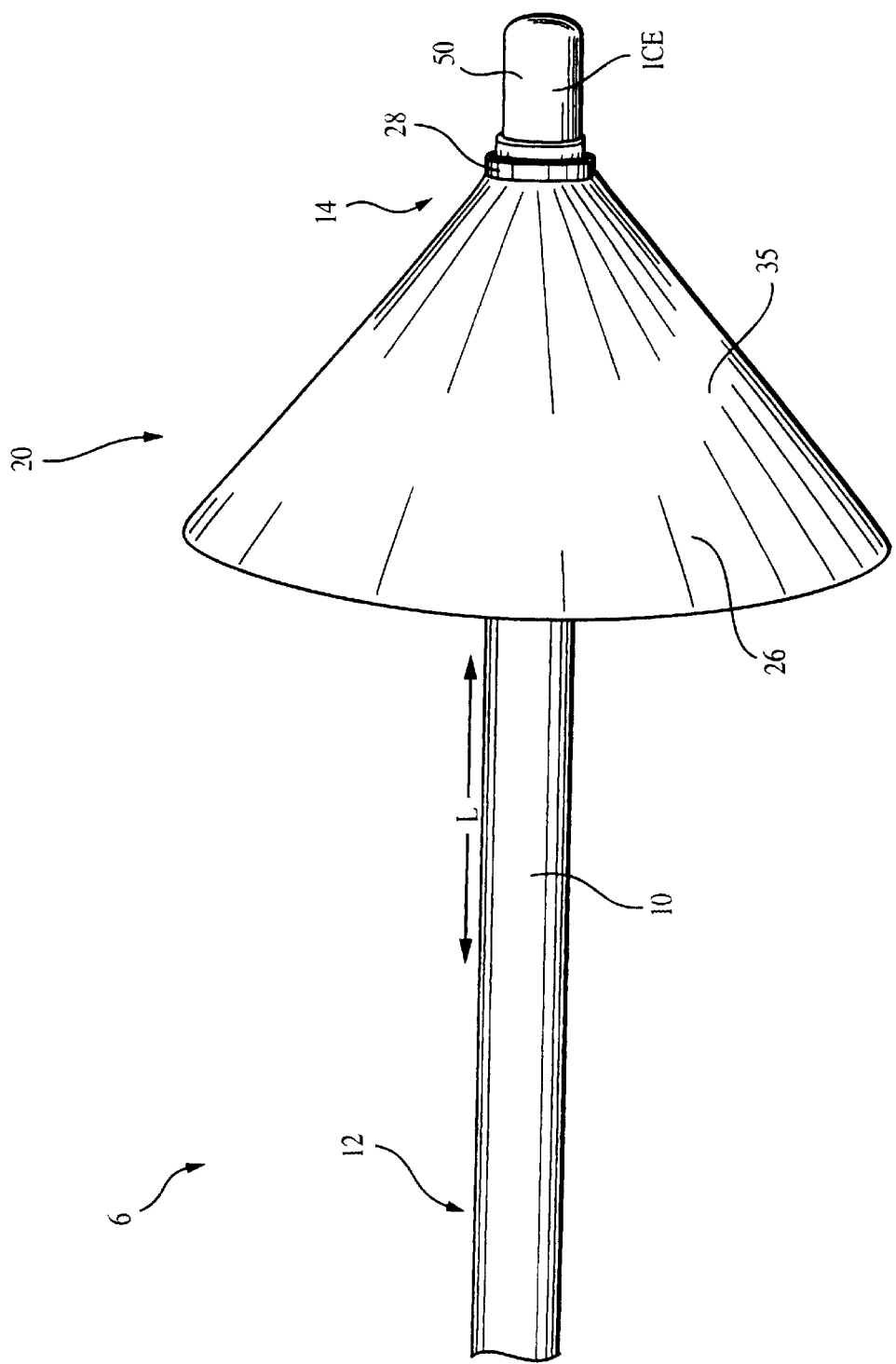
FIG. 5 is an image showing an embodiment of a tissue ablation device of the invention in which the umbrella body includes a membranous material.

Referring to FIG. 5, an embodiment of an ablation device 6 is shown that includes an umbrella body 20 with a membranous material 35 attached to the splines in a manner similar to that of a canopy of an actual umbrella. The membranous material 35 can itself be conductive or ablation elements can be attached to the membranous material. In addition to the embodiment of FIG. 5 showing a solid membranous material, it is to be understood that other structural variants of a membranous material that allow for perfusion flow during deployment of the umbrella body do not depart from the scope of the present invention. A membranous material 35 on an umbrella body such as that shown in FIG. 5 can fold or collapse for retraction in a manner similar to that shown for the umbrella body having hinged loop segments in FIG. 4.

Figure 6A:
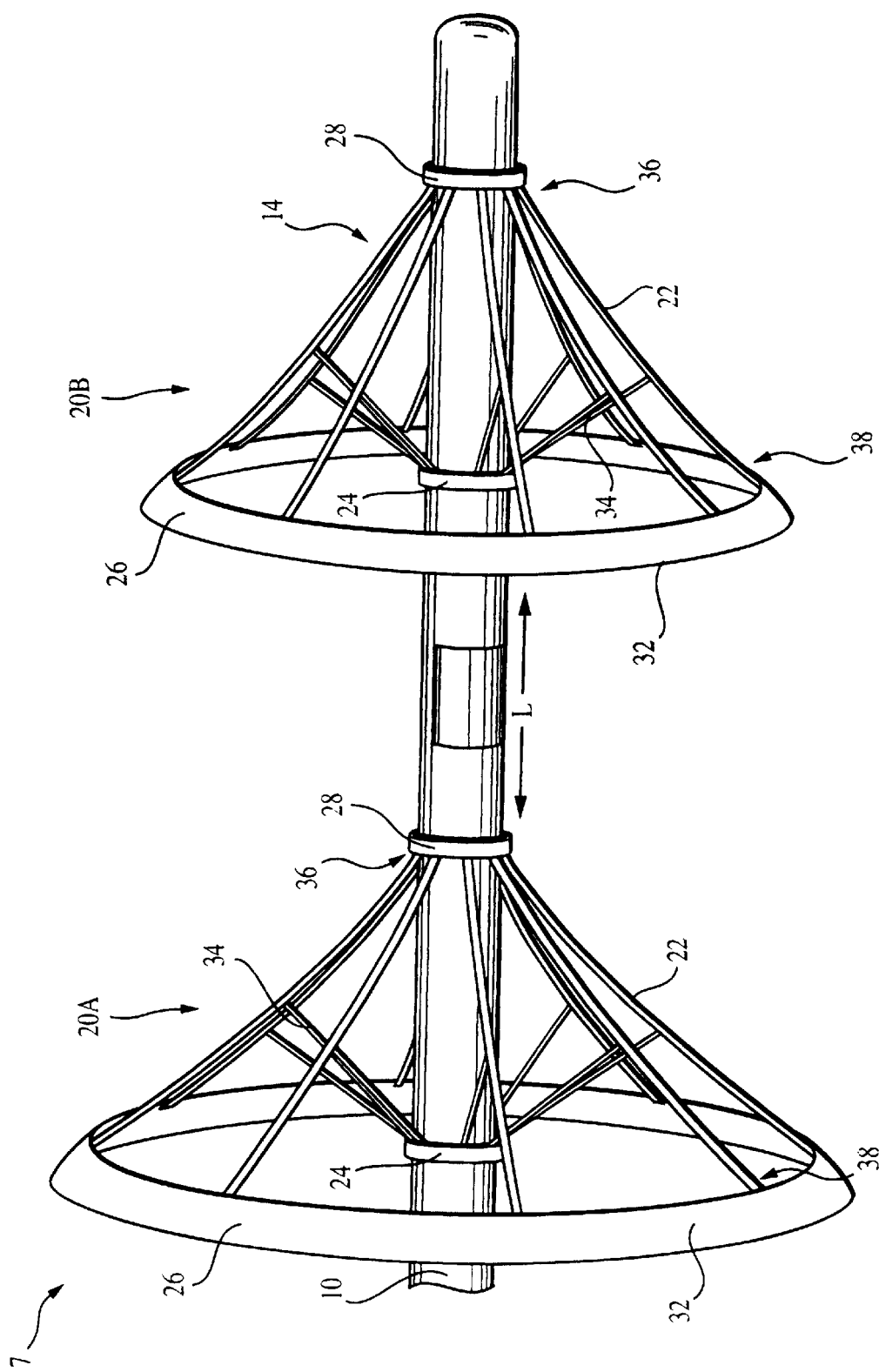
FIGS. 6A and 6B are images showing embodiments of a tissue ablation device of the invention containing two umbrella bodies in which each umbrella body contains a single circumferential loop (FIG. 6A) or multiple circumferential loops (FIG. 6B).
Figure 6B:
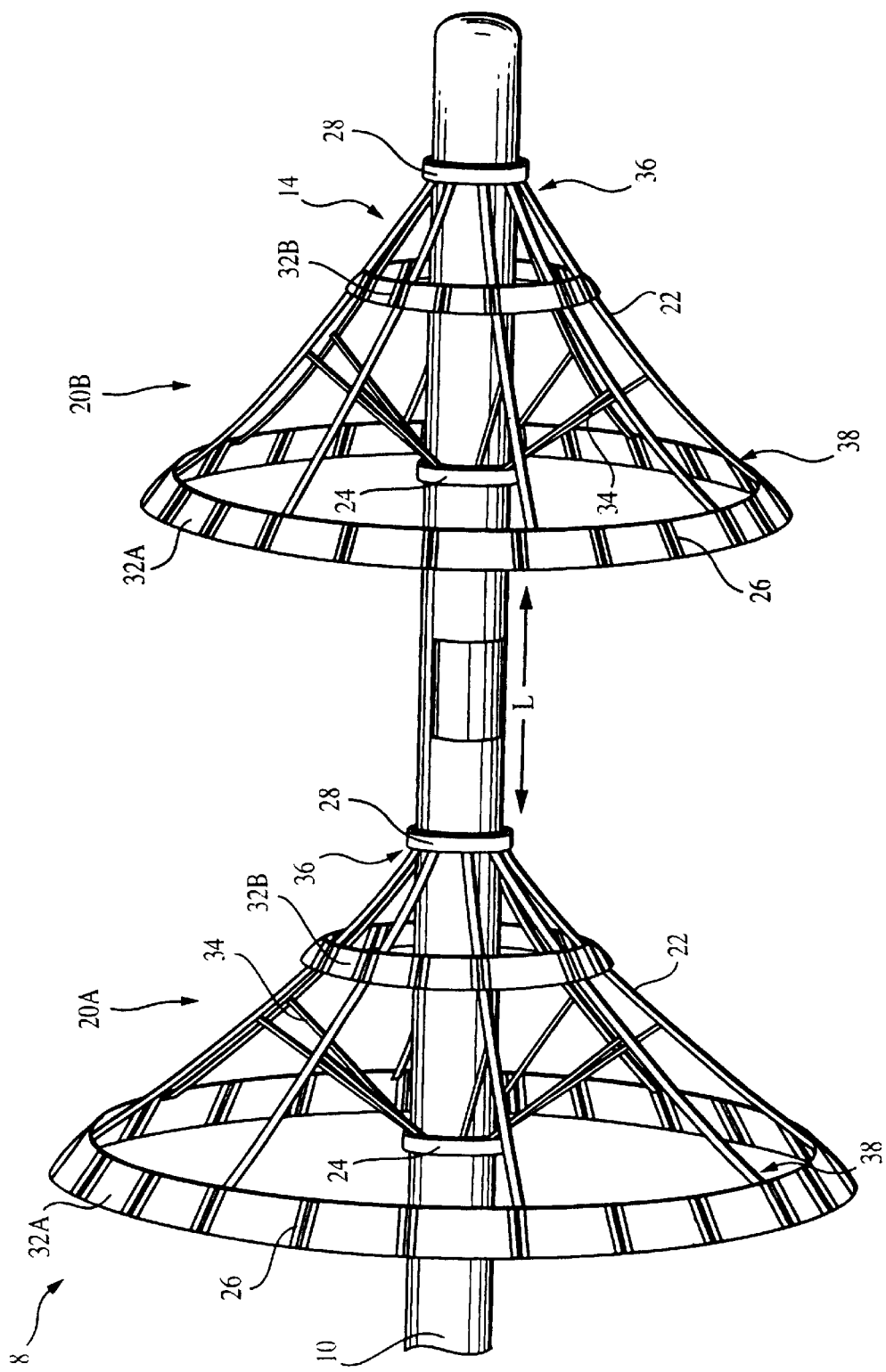

FIGS. 6A and 6B show tissue ablation devices 7, 8 of the invention having more than one umbrella body 20A, 20B. In a device having multiple umbrella bodies, the umbrella bodies can be individually deployed and retracted or can deploy and retract in unison. Referring to FIGS. 6A and 6B, multiple umbrella bodies on a tissue ablation device of the invention can provide an increase in the range of diameters achieved through deployment of umbrella bodies of, for example, different sizes. In addition, multiple umbrella bodies can provide different structural configurations for attaching ablation elements, and provide greater catheter stability during ablation. In addition, multiple umbrella bodies allow for greater lengths of the pulmonary vein muscular sleeve to be monitored for pulmonary vein potentials.

As shown in FIGS. 1A, 2, 3A, 3B, and 5, the tissue ablation device of the invention can optionally include an intracardiac echo (ICE) device 50 for imaging before, during and/or after ablation events. ICE images can also be used to measure pulmonary vein diameter during ablation for early detection of spasm, thrombosis, or stenosis. Other imaging or monitoring devices or elements can be used in addition to or in lieu of an ICE device, and include an ultrasound assembly, or sensing elements such as electrodes. For example, an ultrasound device can be used to produce images of the pulmonary vein such that the ablation elements can be appropriately positioned. Sensing elements also can be used on a tissue ablation device of the invention to measure pulmonary vein potentials before and after ablation. A device 50 can be attached at the end of the distal portion 14 of the catheter body 10. In an embodiment not shown, monitoring and/or imaging devices or elements can be attached to an umbrella body 20 (e.g. splines 22 and/or circumferential loops 32). For example, a particularly useful device is a device having two umbrella bodies (see, for example, FIGS. 6A and 6B) in which elements or devices for imaging or monitoring can be attached to a distal umbrella body 20B for positioning within the pulmonary vein.

Figure 7A:
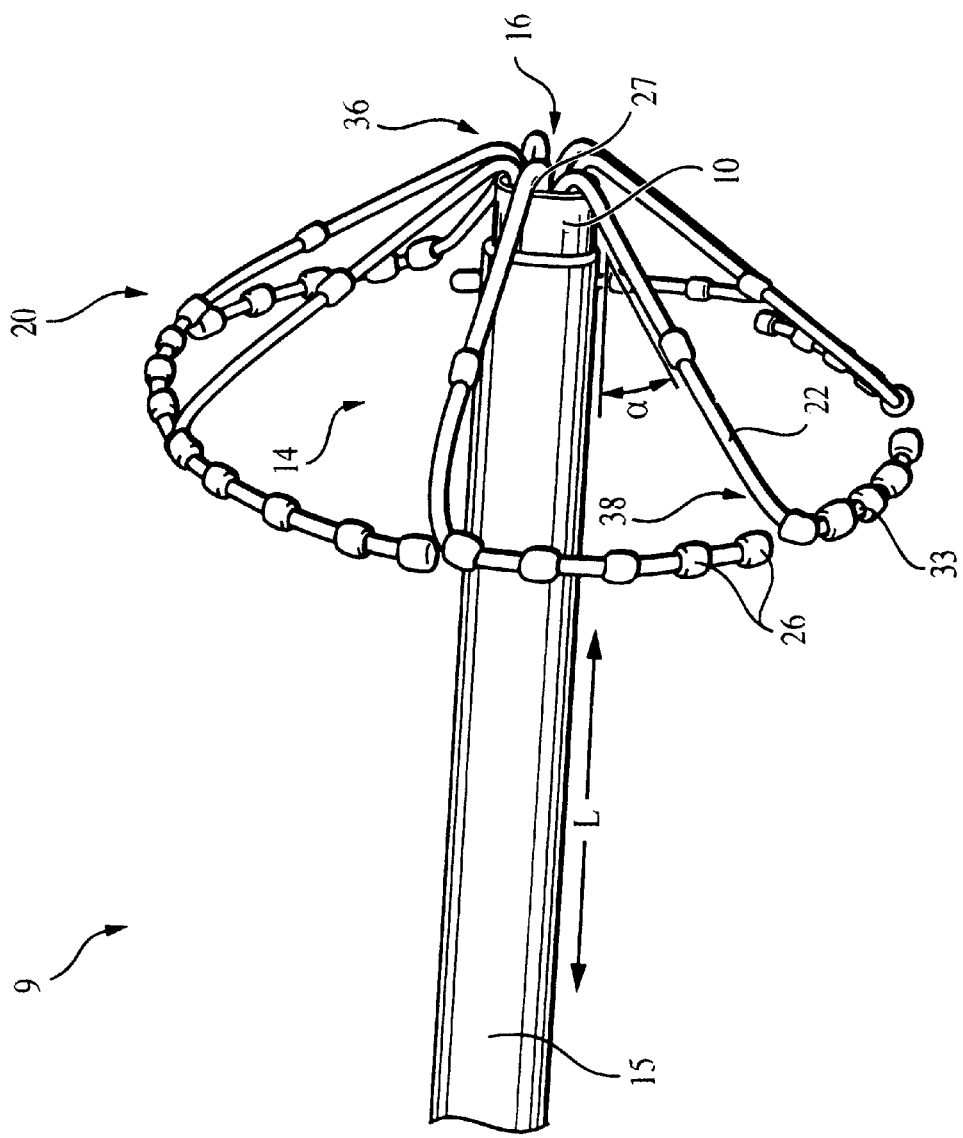
FIGS. 7A–D are images showing an embodiment of a tissue ablation device of the invention in which an umbrella body is shown at representative stages of deployment (FIGS. 7A–B) and at representative stages of retraction (FIGS. 7C–D).
Figure 7B:
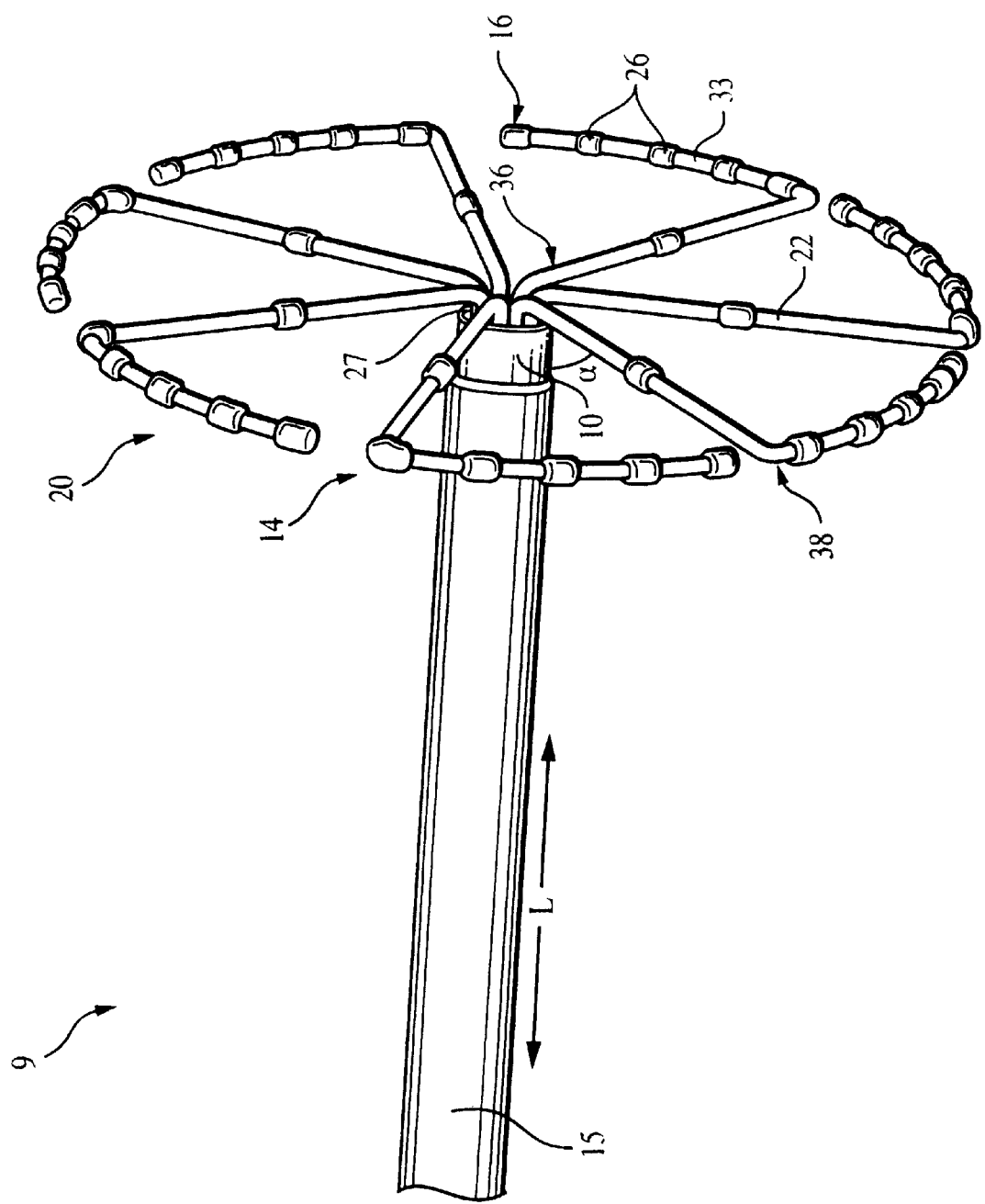
Figure 7C:
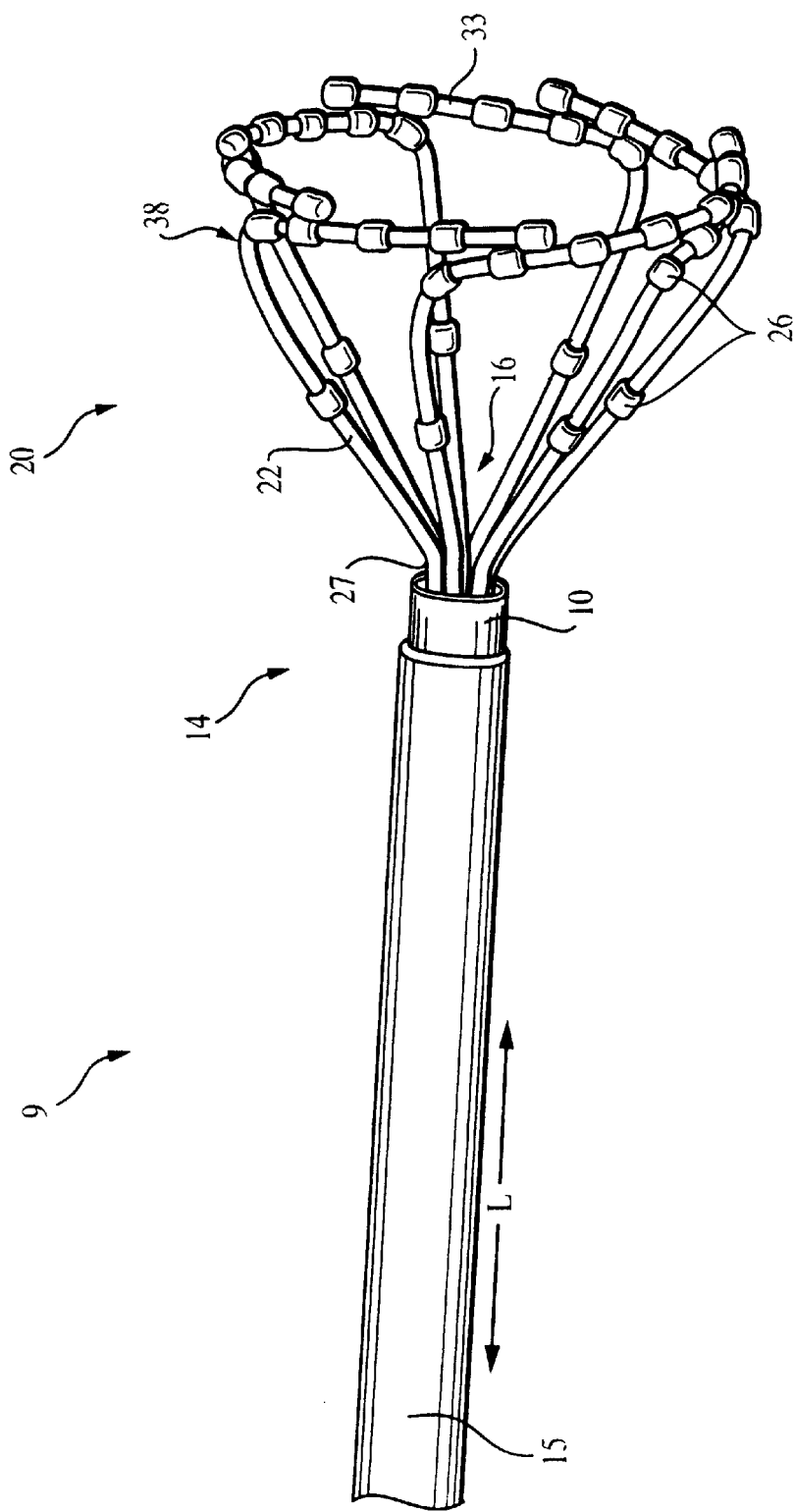

Referring to FIGS. 7A–C, a tissue ablation device 9 is shown having a catheter body 10 and an umbrella body 20 at various stages of deployment and retraction. The catheter body 10 shown in FIGS. 7A–E has a proximal portion 12 and a distal portion 14 creating a longitudinal axis L. The ablation device 9 in FIGS. 7A–E further shows a sheath 15 within which the catheter body 10 can move longitudinally. The sheath 15 can be included as a component of the tissue ablation device 9 or can be a separate guiding sheath used routinely in the art. The umbrella body 20 contains splines 22 having a hinged end 36 and a distal end 38. In this embodiment, the hinged end of the splines are attached to the catheter body via a lip 27 at the distal end 14 of the catheter body 10 between the outside of the catheter body and the central lumen 16 of the catheter body 10. The umbrella body 20 shown in FIGS. 7A–C and 7E includes loop segments 33, wherein each loop segment is contiguous with each spline 22. The umbrella body 20 shown in FIGS. 7A–E additionally contains ablation elements 26 attached to both the splines 22 and to the loop segments 33.

The umbrella body 20 in FIGS. 7A–C and 7E is deployed and retracted through a different mechanism than that described for the umbrella bodies shown in FIGS. 1–6. Instead of deployment being characterized by a radially outward movement of the distal ends of the splines as is shown in FIGS. 1–6, however, the splines 22 of the umbrella body 20 shown in FIGS. 7A–C and 7E emerge from the cental lumen 16 of the catheter body 10 with the distal ends 38 of the splines 22 emerging first. Following deployment of a tissue ablation device 9 as shown in FIGS. 7A–E, a spline 22 can assume an angle α relative to the longitudinal axis L of the catheter body 10 in a manner similar to the splines shown in FIGS. 1–6 (e.g, 0° to 90°). Each spline assumes its desired shape of an umbrella body upon reaching an emerged position on a spline at which the spline can assume such an angle α (e.g., at or near the hinged end of the spline). Splines that deploy and retract in this manner are typically made from Nitinol, but can be made from any material having shape-memory properties. The degree of deployment is determined by the adjustable force placed on the hinged end 36 of the splines 22 by the user at the lip 27 of the distal end 14 of the catheter body 10. The mechanism by which this adjustable force is applied can be a slideable member or members 23 within the central lumen 16 of a catheter body 10 that are attached or contiguous with the hinged end 36 of the splines 22. In this embodiment, the slideable member or members can be configured such that each spline can be manipulated independently to permit greater flexibility in making contact with irregularly shaped pulmonary veins.

Figure 7D:
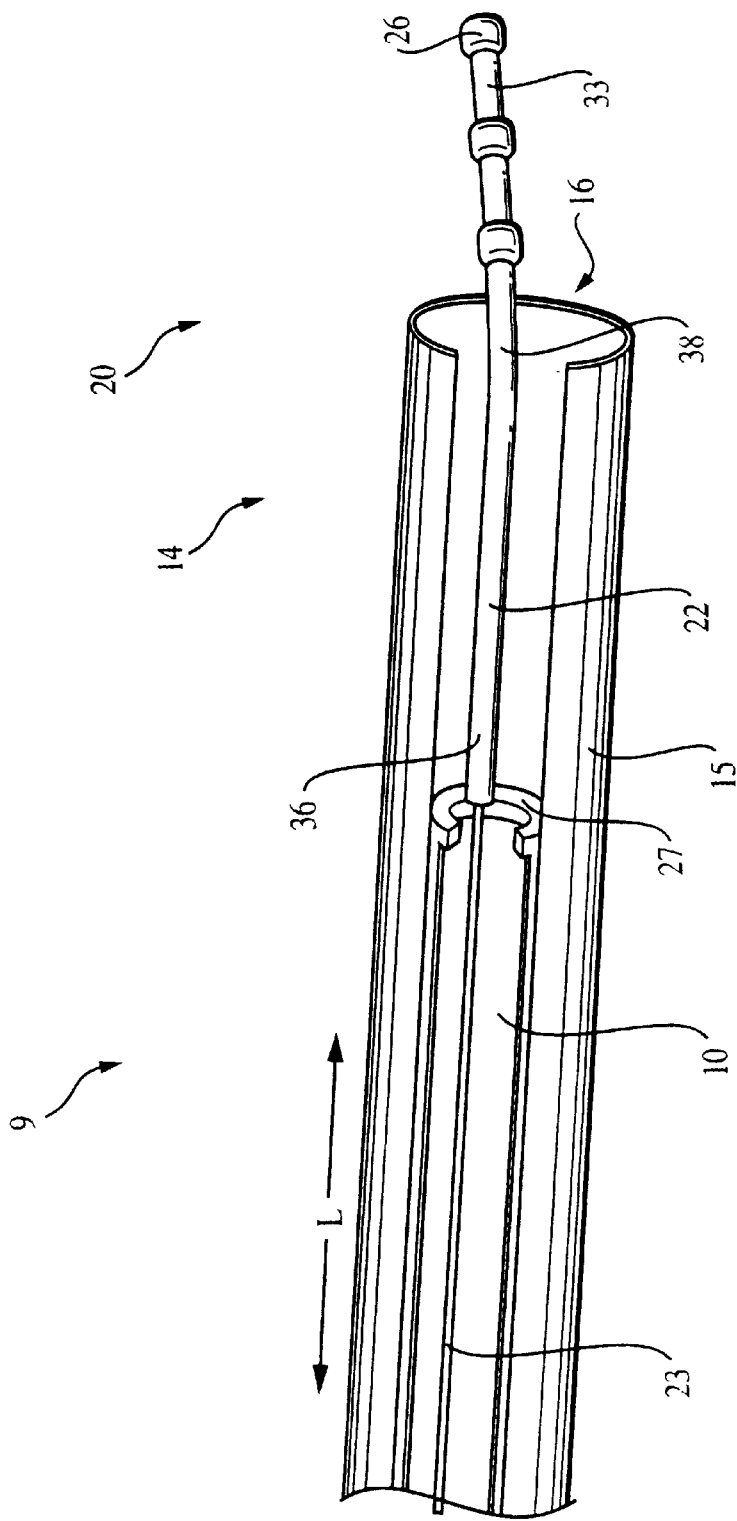
Figure 7E:
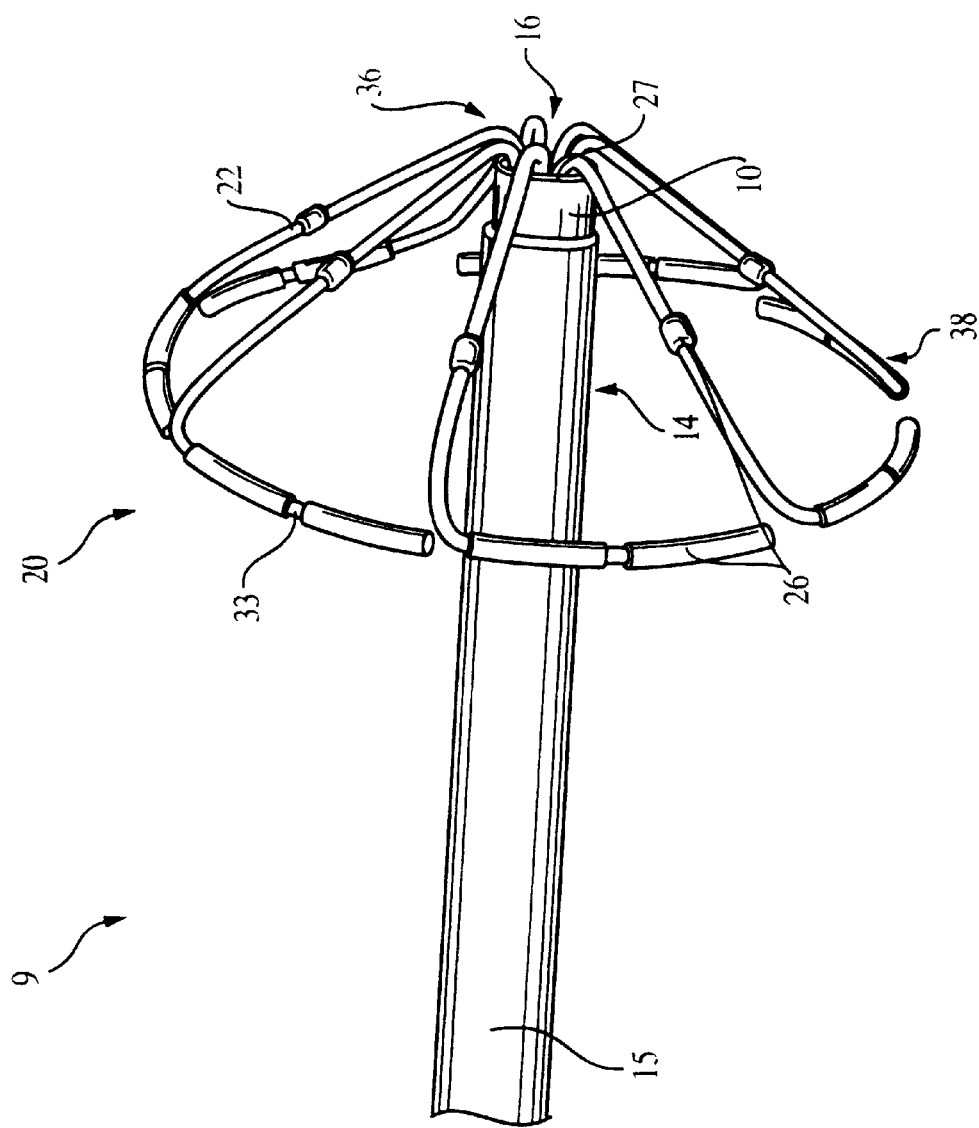
FIG. 7E shows an embodiment of a tissue ablation device in which the size of the electrodes has been increased.

In a retracted position such as the embodiment shown in FIGS. 7A–C, the angle α of each spline is essentially 180° relative to the catheter body (i.e., essentially parallel to the longitudinal axis L of the catheter body) (FIG. 7D). Unlike FIGS. 1–6, however, the distal ends of the retracted splines as shown in FIG. 7D are pointing toward the distal portion of the catheter body (i.e., opposite that of the splines in umbrella bodies shown in FIGS. 1–6) and are internal to the catheter body (i.e., within the central lumen). Retraction of the umbrella body 20 following deployment can be obtained by retraction of the splines 22 and loop segments 33 back into the central lumen 16 of the catheter body 10 or, alternatively, a catheter body 10 or sheath 15 can be advanced over the splines 32 and loop segments 33 to affect retraction of the umbrella body 20.

As used herein, the term "deployment element" refers to the components of a catheter body that are necessary for or function in deployment of an umbrella body. Deployment elements can include any or all of the following: a component of the umbrella body necessary for deployment of the umbrella body (e.g., a slideable deployment/retractor collar 24, or connector rods 34); connectors that connect the components of the umbrella body necessary for deployment of the umbrella body with a mechanism at the proximal portion of the catheter body that is manipulated by a user to affect deployment of the umbrella body (e.g., wires); and a mechanism at the proximal portion of the catheter body that is manipulated by a user to affect deployment of the umbrella body. Umbrella bodies can be deployed in a number of fashions, and it is understood that deployment elements are not limited to those shown in the embodiments herein. The deployment elements described above can, but does not necessarily include means for retracting the umbrella body.

The umbrella body of a tissue ablation device of the invention is generally in a retracted position for percutaneous translumenal delivery into the left atrium. Deployment of the umbrella body (as shown in FIGS. 1–7 or as can be contemplated from the description herein) allows for ablation elements to circumferentially engage target tissue having a range of diameters. As discussed herein, target tissue refers to a pulmonary vein ostium. The umbrella body, however, can be configured for engaging other tissues. In addition to pulmonary vein ostia, target tissues can include, for example, other venous structures such as the superior vena cava or the coronary sinus, and also can include non-cardiac target tissue such as cervical tissue.

A method for using a tissue ablation device of the invention in treating atrial arrhythmias includes inserting and advancing the distal end of a catheter body into the vasculature of an individual experiencing atrial arrhythmia; positioning an umbrella body or bodies attached to the distal end of the catheter body such that upon deployment, the splines of the umbrella body are circumferentially disposed at the pulmonary vein ostium; and thereafter ablating a region of tissue at the pulmonary vein ostium using ablation elements attached to the umbrella body.

Inserting and advancing a catheter into the atrium of a heart are well-known and routine techniques used in the art. A catheter is generally introduced and advanced into the vasculature of an individual using one or more guiding sheaths. Guiding sheath designs for use in ablation procedures in both the right and/or left atrial chambers are disclosed in U.S. Pat. Nos. 5,427,119; 5,497,119; 5,564,440; and 5,575,766. The "Seldinger" technique is routinely used for introducing a sheath such that a catheter can be advanced into the right venous system of an individual. Advancing a catheter into the left atrium from the right vasculature requires traversing the septal wall. A transseptal puncture is generally performed using a "Brochenbrough" needle or trocar in an art-known procedure. It is contemplated, however, that other methods for introducing a tissue ablation device of the invention into the left atrium are suitable and include, for example, a retrograde approach or a venous cut-down approach. See, for example, U.S. Pat. No. 6,254,599 for a detailed description of procedures used in the art to access the left atrium.

Figure 8:
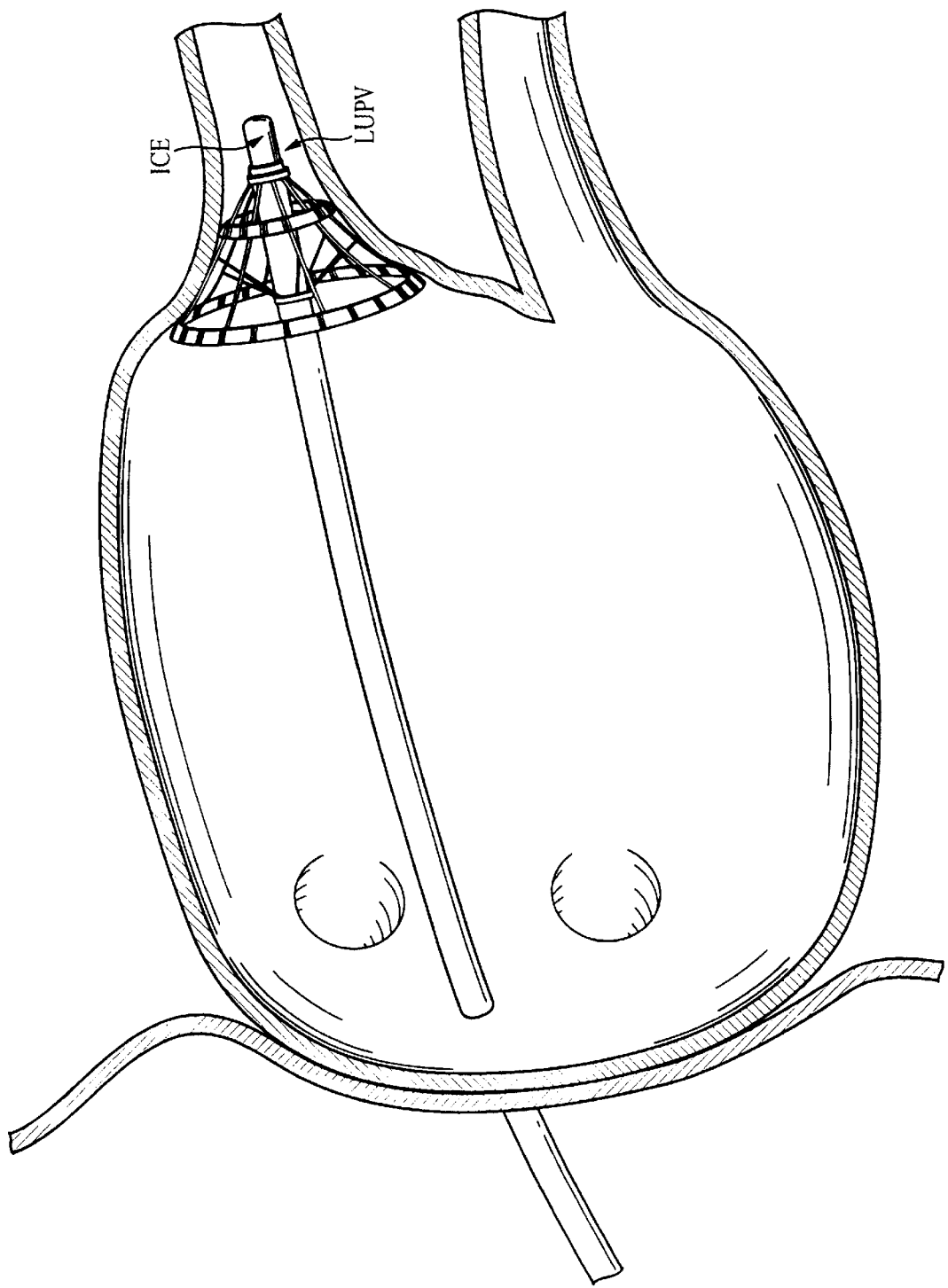
FIG. 8 is a perspective view of a left atrium showing approximate positioning of a tissue ablation device of the invention in which the umbrella body has been deployed.

Circumferential ablation at the pulmonary vein ostium can electrically isolate or disrupt the rapid firing foci located predominantly inside the pulmonary vein that causes the fibrillation. Circumferential ablation also can be performed at the ostium of a pulmonary vein to reduce the risk of pulmonary vein stenosis due to ablation within the pulmonary vein. Furthermore, ablation can be limited to single or multiple loop segments to further minimize the risk of stenosis. To contact the pulmonary vein ostium with the tissue ablation device of the invention, the umbrella body is positioned just outside of the ostium to be ablated. As used herein, "ostium" generally refers to the junction between the left atrium and the pulmonary vein. As the size of each pulmonary vein varies, as does the angle of transition from the atrium into each vein, the size of each ostium (i.e., the size of the junction) varies. Following deployment or partial deployment of the umbrella body, the catheter body is advanced into the pulmonary vein ostium such that the splines and/or the circumferential loop or loop segments circumferentially engage target tissue at an ostium (see, for example, FIG. 8). Given that the degree of deployment is adjustable, the umbrella body can be manipulated at the ostium to ensure that the target tissue has been fully engaged with the umbrella body (e.g., at positions where ablation elements are attached to the umbrella body).

Following appropriate positioning, the ablation elements are energized to a sufficient level to ablate the contacted tissue. In one embodiment in which radiofrequency signals are used to generate heat at the site of ablation, the pulmonary vein ostium can be ablated for 30–120 seconds at a temperature of about 40° C. to about 70° C. As a result, a lesion pattern is formed in the tissue that is dependent upon the pattern of ablation elements energized. The lesion pattern is generally formed in a plane that is substantially perpendicular to the longitudinal axis of the catheter body. Advantageously, a lesion pattern can be formed within a portion of the pulmonary vein ostium having a larger diameter (e.g., on the atrial side of the junction) or a smaller diameter (e.g., on the pulmonary vein side of the ostium). In addition, the lesion pattern can be formed around the entire circumference of the ostium, or only at focal or segmental sections found to have pulmonary vein potentials.

A tissue ablation device of the invention can be configured to additionally monitor electrical signals along the pulmonary vein and pulmonary vein ostium before and after ablation. Signals within the pulmonary vein can be monitored prior to ablating to localize an arrhythmogenic origin of the atrial arrhythmia and determine the best location to ablate and produce a conduction block. In addition, signals from within the pulmonary vein can be monitored during ablation. In addition, ultrasound imaging of the pulmonary vein can be performed via an ICE device during ablation. Imaging pulses such as ultrasound waves can be emitted in an alternating fashion with the energy-emitting signals from the ablation elements. Thus, using pulsed ultrasound and pulsed ablation signals that are out of phase, images that are free from ablation energy interference can be performed during an ablation procedure. Alternating ablation and sensing can improve signal reception for monitoring purposes and, in addition, can be used to continually adjust the site(s) of ablation to correspond with the focal origin of the arrhythmia or to correspond to a position between the focal origin and the atrium in order to block aberrant conduction from the origin and into the atrial wall. Electrical signals along the pulmonary vein wall may also be monitored subsequent to circumferential ablation to determine the efficacy of the tissue ablation in forming a complete conduction block against arrhythmogenic conduction. Pacing also can be performed from elements attached to a distal or proximal umbrella body to determine whether conduction is present or whether the vein has been electrically isolated.

In tissue ablation devices that use, for example, radiofrequency electrodes for energy delivery, alternating the energy-emitting signals from the ablation elements with the signal reception for monitoring can result in less tissue damage due to direct electrical disruption of cell membranes and due to heat. For example, at the onset of ablation, a thin rim of surface tissue at the site of ablation is rapidly heated, while the deeper tissues at the same site are heated at a slower rate by conduction. Once the energy-emitting signal is terminated, the surface tissue cools rapidly by the circulating blood (as well as by conductive loss). The temperatures at the deeper tissues cool far more slowly. Since the surface is cool, another energy-emitting signal can be applied. Such amplitude modulated energy delivery can optimize the natural convective cooling that occurs at the electrode-tissue interface. In addition, since the energy-emitting signal is brief, higher levels of energy than could otherwise be delivered can be applied, resulting in a larger area of ablated tissue. For example, steady state thermal equilibrium using amplitude modulated radiofrequency waves can be achieved in 5–20 seconds at 500 kHz. Since high-energy short-duration pulses can be associated with arcing and coagulum formation of the tissue, amplitude modulation can be an alternative to the waveforms currently used in the art. Amplitude modulation can decrease the incidence of impedance rises permitting longer energy deliveries and greater total energy transmittal to the deeper tissues.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A tissue ablation device comprising:
   a catheter body, wherein said catheter body has a proximal portion and a distal portion, wherein said proximal and distal portions define a longitudinal axis; and
   at least one deployable umbrella body attached to the distal portion of the catheter body, wherein the umbrella body comprises:
      a plurality of radial splines, each of said splines having a distal end and a hinged end, wherein said hinged end is attached to said catheter body, at least one ablation element, wherein said at least one ablation element is attached to at least one of said plurality of splines, and at least one circumferential loop or loop segment attached to said plurality of splines.

2. The tissue ablation device of claim 1, further comprising a deployment element connected to the splines, wherein the deployment element is capable of adjustably deploying the umbrella body.

3. The tissue ablation device of claim 1, wherein said ablation elements are attached to said splines at said distal end of said splines.

4. The tissue ablation device of claim 1, wherein said ablation elements are attached to said splines at a position medial to said distal end and said hinged end of said spline.

5. The tissue ablation device of claim 2 wherein the deployment element comprises a slideable deployment/retractor collar that circumscribes the splines.

6. The device of claim 1, wherein the hinged end of the splines is attached to the catheter body.

7. The device of claim 1, wherein the hinged end of the splines is attached to a central hub on the catheter body.

8. The tissue ablation device of claim 5, further comprising connector rods linking said slideable deployment/retractor collar to said splines.

9. The tissue ablation device of claim 1, wherein said umbrella body comprises one circumferential loop attached to said plurality of splines.

10. The tissue ablation device of claim 1, wherein said umbrella body comprises two circumferential loops attached to said plurality of splines.

11. The tissue ablation device of claim 1, wherein said loop segment is contiguous with said spline.

12. The tissue ablation device of claim 1, wherein said loop segments are hinged.

13. The tissue ablation device of claim 1, wherein at least one of said circumferential loops or loop segments is conductive.

14. The tissue ablation device of claim 1, further comprising ablation elements attached to at least one of said circumferential loops or loop segments.

15. The tissue ablation device of claim 1, wherein the distal ends of said splines move through an angle α relative to the longitudinal axis of said catheter body.

16. The tissue ablation device of claim 15, wherein said angle α is between about 0° and about 90° relative to the longitudinal axis of said catheter body.

17. The tissue ablation device of claim 15, wherein said angle α is between about 0° and about 180° relative to the longitudinal axis of said catheter body.

18. The tissue ablation device of claim 1, wherein said umbrella body further comprises membranous material attached to one or more sets of adjacent splines.

19. The tissue ablation device of claim 18, wherein said membranous material comprises at least one ablation element.

20. The tissue ablation device of claim 18, wherein said membranous material is conductive membranous material.

21. The tissue ablation device of claim 1, wherein said ablation element is selected from a cryogenic element, an ultrasound element, an light-emitting element, a microwave element, a thermal element, a laser, chemical fluid, and an electrode element.

22. The tissue ablation device of claim 1, wherein said ablation element is an electrode.

23. The tissue ablation device of claim 22, wherein said electrode is a band electrode.

24. The tissue ablation device of claim 22, wherein said electrode is a spiral electrode.

25. The tissue ablation device of claim 22, wherein said electrode is a coil electrode.

26. The tissue ablation device of claim 1, wherein said device comprises one umbrella body.

27. The tissue ablation device of claim 1, wherein said device comprises two umbrella bodies.

28. The tissue ablation device of claim 1, further comprising at least one of a monitoring device or a sensing element.

29. The tissue ablation device of claim 28, wherein said monitoring device is an intracardiac echo device attached to said tissue ablation device.

30. The tissue ablation device of claim 28, wherein said monitoring device is an ultrasound transducer assembly attached to said tissue ablation device.

31. The tissue ablation device of claim 28, wherein said sensing elements are electrodes.

32. The tissue ablation device of claim 2, wherein said deployment element comprises a slideable deployment/retractor collar that circumscribes the splines, the collar further comprising an apparatus for adjustably sliding said deployment/retractor collar along the longitudinal axis of said catheter body.

33. The tissue ablation device of claim 2, wherein said deployment element comprises a slideable member, wherein said slideable member is contiguous with said splines, wherein said slideable member is within a central lumen of said catheter body.

34. A tissue ablation device for treating atrial arrhythmia, comprising
    a catheter body, wherein said catheter body has a proximal portion and a distal portion, wherein said proximal and distal portions define a longitudinal axis;
    at least one deployable umbrella body located at the distal portion of the catheter body, wherein the umbrella body comprises:
        a plurality of splines attached to said catheter body, at least one ablation element, wherein said at least one ablation element is attached to at least one of said plurality of splines, and at least one circumferential loop or loop segment attached to said plurality of splines.

35. The device of claim 34, wherein the splines may be radially deployed to fit the size of the pulmonary vein ostium.

36. A method for treating arrhythmia, comprising:
    providing a tissue ablation device, wherein said device comprises:
        a catheter body with a proximal portion and a distal portion, wherein said proximal and distal portions define a longitudinal axis;
        at least one deployable umbrella body attached to the distal portion of the catheter body, wherein the umbrella body comprises a plurality of splines attached to said catheter body, and at least one ablation element, wherein said at least one ablation element is attached to at least one of said plurality of splines, wherein the umbrella body is adapted to be delivered to a patient's vasculature in a retracted configuration and is adapted to contact a circumferential region of tissue at a pulmonary vein ostium in a deployed configuration; and
    inserting and advancing the distal end of the catheter body into the vasculature of an individual experiencing arrhythmia;
    positioning and deploying the umbrella body such that the plurality of splines are circumferentially disposed at the tissue of a pulmonary vein ostium; and
    activating the ablation element.

37. The method of claim 36, wherein said arrhythmia is selected from atrial fibrillation, atrial tachycardia, and atypical atrial flutters.

38. The method of claim 36, wherein the arrhythmia originates at least in part from an arrhythmogenic origin located at or near the pulmonary vein ostium or other venous structure.

39. The method of claim 36, wherein said ablation element is an element selected from the group consisting of a cryogenic element, an ultrasound element, a light-emitting element, a microwave element, a thermal element, a laser, chemical fluid, and an electrode element.

40. The method of claim 36, wherein said ablation element is an electrode.

41. The method of claim 40, wherein said electrode delivers a radiofrequency signal.

42. The method of claim 40, wherein said electrode delivers a 500 KHz radiofrequency signal.

43. The method of claim 40, wherein said electrode delivers a 250 KHz radiofrequency signal.

44. The method of claim 40, wherein said electrode delivers a radiofrequency signal for about 30 to about 120 seconds.

45. The method of claim 40, wherein said electrode delivers a radiofrequency signal at a temperature of about 40° C. to about 70° C.

46. The method of claim 36, wherein said activation of said ablation element is a focal activation.

47. The method of claim 36, wherein said activation of said ablation element is a segmental activation.

48. The method of claim 36, wherein said activation of said ablation element is circumferential activation.

49. The method of claim 36, further comprising a monitoring device or sensing elements.

50. The method of claim 36, wherein signals emitted from said monitoring device or sensing elements are out of phase with signal emitted from said ablation elements.

* * * * *

UNITED STATES PATENT AND TRADEMARK OFFICE
CERTIFICATE OF CORRECTION

PATENT NO. : 6,669,693 B2
DATED : December 30, 2003
INVENTOR(S) : Paul A. Friedman It is certified that error appears in the above-identified patent and that said Letters Patent is hereby corrected as shown below:

Column 13,
Line 50, please delete "an".

Signed and Sealed this

Twenty-fourth Day of February, 2004

JON W. DUDAS
*Acting Director of the United States Patent and Trademark Office*